United States Patent [19]  
Evans et al.

[11] Patent Number: 4,870,169  
[45] Date of Patent: Sep. 26, 1989

[54] INTERMEDIATES FOR BETA-LACTAM ANTIBIOTICS

[75] Inventors: David A. Evans, Concord; Eric B. Sjogren, Arlington, both of Mass.

[73] Assignee: President and Fellows of Harvard College, Cambridge, Mass.

[21] Appl. No.: 184,857

[22] Filed: Apr. 22, 1988

Related U.S. Application Data

[62] Division of Ser. No. 99,032, Sep. 21, 1987, which is a division of Ser. No. 13,521, Feb. 11, 1987, Pat. No. 4,734,495, which is a division of Ser. No. 755,982, Jul. 17, 1985, Pat. No. 4,665,171.

[51] Int. Cl.$^4$ .................... C07D 263/38; A61K 31/42
[52] U.S. Cl. ..................... 540/229; 540/225
[58] Field of Search ........... 548/226, 225, 229

[56] References Cited

U.S. PATENT DOCUMENTS

| | | | |
|---|---|---|---|
| 4,186,129 | 1/1980 | Huth | 548/229 |
| 4,588,694 | 5/1986 | Hamaguchi et al. | 435/280 |
| 4,665,171 | 5/1987 | Evans et al. | 540/364 |
| 4,772,694 | 9/1988 | Cooper | 548/225 |

OTHER PUBLICATIONS

Evans, D. A., et al., "Asymmetric Alkylation Reactions of Chiral Imide Enolates", *J. Am. Chem. Soc.*, 1982, 104, 1737–1739.
Evans, D. A., et al., "Enantioselective Aldol Condensations. 2.", *J. Am. Chem. Soc.*, 1981, 103, 2127–2129.
Close, W. J., "Anticonvulsant Drugs. IV. Some 2-Oxazolidones", *J. Am. Chem. Soc.*, 1951, 73, 95.
Pirkle, W. H., et al., *J. Org. Chem.*, vol. 48, No. 15 (1983), pp. 2520–2527.

*Primary Examiner*—Nicholas S. Rizzo
*Attorney, Agent, or Firm*—William B. Scanlon; Leroy Whitaker

[57] ABSTRACT

1-Benzyl(or substituted benzyl)-3β-[4(S)-aryloxazolidin-2-one-3-yl]-4β-(2-arylvinyl)azetidin-2-ones are provided via cycloaddition of a 4(S)-aryloxazolidin-2-one-3-ylacetyl halide and an imine formed with a benzylamine and a 3-arylacrolein, e.g. cinnamaldehyde. The azetidinones are useful chiral intermediates in an asymmetric synthesis of 1-carba(1-dethia)-3-hydroxy-3-cephem-4-carboxylic acids and esters and to monocyclic β-lactam antibiotics.

4 Claims, No Drawings

INTERMEDIATES FOR BETA-LACTAM ANTIBIOTICS

This application is a division of application Ser. No. 099,032 filed Sept. 21, 1987, a division of application Ser. No. 13,521, filed Feb. 11, 1987, now U.S. Pat. No. 4,734,495, which was a division of application Ser. No. 755,982 filed July 17, 1985, now U.S. Pat. No. 4,665,171.

BACKGROUND OF THE INVENTION

The United States government has rights in this invention by virtue of grant No. GM-33328 awarded by the National Institutes of Health.

This invention relates to a process for the preparation of 1-carba(1-dethia)-3-cephem-4-carboxylic acids and derivatives thereof. In particular, it relates to an asymmetric process for the preparation of 1-carba(1-dethia)-3-cephem-4-carboxylic acids and to 1-substituted-3β-(4(S)-aryloxazolidin-2-one-3-yl)-4β-styryl (or substituted styryl)azetidin-2-one intermediates useful therein. Related 4-substituted 3β-(4(S)-aryloxazolidin-2-one-3-yl)azetidin-2-one compounds, useful in the asymmetric synthesis of other β-lactam antibiotics, are provided.

The 1-carba(1-dethia)-3-cephem-4-carboxylic acids, hereinafter 1-carbacephalosporins, possess the 4,6 bicyclic ring system represented by the following structural formula

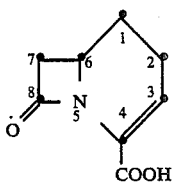

wherein the arbitrary numbering system employed according to the cepham nomenclature system is used for convenience as indicated.

The preparation of 1-carbacephalosporanic acids and C-3 substituted methyl derivatives thereof is taught broadly by Christensen et al., U.S. Pat. No. 4,226,866. Hirata et al., U.K. Patent Application No. 2041923 teach a process for preparing 3-halo and 3-H 1-carbacephalosporins; and Hatanaka et al., Tetrahedron Letters, Vol. 24, No. 44, pp 4837–4838 (1983), teach a process for preparing a 3-hydroxy-(±)-1-carbacephalosporin.

The 1-carbacephalosporins thus far have not been obtained from natural sources, for example, as microbial metabolites. Accordingly methods for the total synthesis of these promising compounds are highly desirable, particularly methods which are adaptable to large scale manufacture.

SUMMARY

1-Substituted-3β-[4(S)-aryloxazolidin-2-one-3-yl]-4β-(2-arylvinyl)azetidin-2-ones are prepared via cycloaddition of a 4(S)-aryloxazolidin-2-one-3-ylacetyl halide with an imine formed with a benzylamine and a 3-arylacrolein, eg. cinnamaldehyde. A preferred intermediate, 1-benzyl-3β-(4(S)-phenyloxazolidin-2-one-3-yl)-4β-(3-methoxystyryl)azetidin-2-one, is converted asymmetrically to 1-carbacephalosporins as follows. The 4β-(3-methoxystyryl)substituted azetidinone is first hydrogenated to the corresponding 4β-[2-(3-methoxyphenyl)ethyl]azetidinone and lithium-ammonia reduction of the latter in the presence of t-butyl alcohol provides 3β-amino-4β-[2-(5-methoxycyclohex-1,4-dienyl)ethyl]azetidinone. Following protection of the 3-amino group of the reduction product the diene is oxidized with ozone to form the β-keto ester, methyl 5-[3β-(protected amino)azetidin-2-one-4-yl]-3-oxopentanoate. The β-keto ester is converted to the 4-diazo-3-oxopentanoic acid methyl ester via diazo transfer and the latter is cyclized with Rhodium II to the 7β-protected amino-3-hydroxy-1-carbacephalosporin-4-carboxylic acid methyl ester. Alternatively, the diazo β-keto methyl ester is converted to an ester more readily removed, eg. the diazo β-keto benzyl ester, via trans-esterification with titanium tetraisopropoxide and a benzyl alcohol. The 7-protected amino 3-hydroxy 1-carbacephalosporin can be deprotected, acylated with the desired carboxylic acid, reacted with diazomethane and then deesterified to provide the desired 7β-acylamino-3-methoxy-1-carbacephalosporin-4-carboxylic acid antibiotic.

Other 1-substituted 3β-(4(S)-aryloxazolidin-2-one-3-yl)-4β-substituted azetidin-2-ones are useful intermediates to monocyclic β-lactam antibiotics such as the monobactam acids.

DETAILED DESCRIPTION

The 3β-(4(S)-aryloxazolidin-2-one-3-yl)azetidin-2-one intermediates provided by this invention are represented by the following formula 1

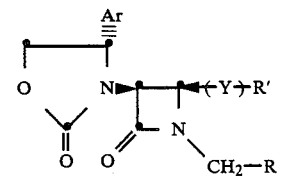

wherein Ar is phenyl, $C_1$–$C_4$ alkylphenyl, halophenyl, $C_1$–$C_4$ alkoxyphenyl, naphthyl, thienyl, furyl, benzothienyl, or benzofuryl; R is phenyl, $C_1$–$C_4$ alkylphenyl, $C_1$–$C_4$ alkoxyphenyl, or halophenyl; Y is —CH=CH—, or —$CH_2$—$CH_2$—; and R' is phenyl, $C_1$–$C_4$ alkylphenyl, $C_1$–$C_4$ alkoxyphenyl, halophenyl, furyl or naphthyl.

Preferred azetidinones are represented by the formula 1 wherein Ar and R are phenyl or substituted phenyl, and R' is phenyl, substituted phenyl, or furyl. Examples of such preferred compounds are 1-benzyl-3β-[4(S)-phenyloxazolidin-2-one-3-yl]-4β-styrylazetidin-2-one, 1-benzyl-3β-[4(S)-phenyloxazolidin-2-one-3-yl]-4β-(3-methoxystyryl)azetidin-2-one, and 1-benzyl-3β-[4(S)-phenyloxazolidin-2-one-3-yl]-4β-[2-(2-furyl)ethenyl]azetidin-2-one.

The azetidinones represented by the formula 1 are obtained by the cycloaddition of a 4(S)-aryloxazolidin-2-one-3-ylacetyl halide and an imine formed with a benzylamine and a 3-arylacrolein. The acid halide is converted in situ with a trialkylamine to the corresponding homochiral ketene. The ketene and imine upon cycloaddition provide the azetidinone. Alternatively, the ketene can be generated with the anhydride of the oxazolidinone acetic acid and trifluoroacetic acid, or with phosphoryl chloride or phosphoryl bromide. The cycloaddition reaction is a key step in the asymmetric process of this invention for the preparation of 1-carba-(1-dethia)cephalosporins as described hereinafter.

The 4(S)-aryloxazolidin-2-one-3-ylacetyl halide employed in the cyclization is obtained with an L-arylglycine represented by the formula 1a

1a wherein Ar has the same meanings as defined for formula 1. The preparation is illustrated in the following reaction scheme.

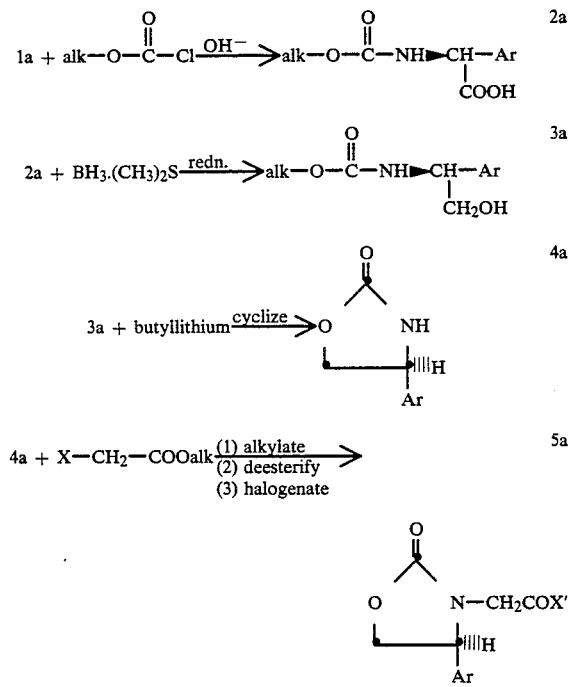

In the above scheme "alk" refers to $C_1$-$C_4$ alkyl eg. methyl, ethyl, n-propyl, and t-butyl; X refers to halogen, preferably chloro or bromo; X' is chloro, bromo, trifluoroacetoxy, or $-OP(=O)X_2$ wherein X is halogen; and AR has the same meanings as previously defined.

In carrying out the preparation of the 4-aryloxazolidinone 4a the L-arylglycine is first converted to the carbmate 2a. The arylglycine is dissolved in aqueous base by utilizing only the amount of base needed to form the soluble salt plus a small excess. The solution is cooled to a temperature between about 0° C. and about 10° C. and non-stoichiometric amounts of the haloformate are added in several portions with stirring. Additional base is added to redissolve the arylglycine and additional haloformate is added portionwise with stirring. This process is repeated in the cold until an excess of the stoichiometric amount of haloformate has been added and carbamate formation is completed. The reaction is preferably carried out as rapidly as possible. Bases such as the alkali metal hydroxides, eg. sodium hydroxide and potassium hydroxide are best used. Preferably 3N sodium hydroxide is used. The L-carbamate derivative 2a is recovered from the reaction mixture by acidification and extraction of the precipitated carbamate with a water immiscible solvent eg. a halogenated hydrocarbon solvent such as dichloromethane.

The L-carbamate 2a is reduced with excess borane-dimethylsulfide in tetrahydrofuran at a temperature between about 20° C. and about 40° C. to provide the L-alcohol 3a. The borane-dimethylsulfide reagent is added to a solution of the carbamate acid in tetrahydrofuran cooled to about 0° C. and the mixture is stirred at the temperature range, conveniently at room temperature, for about 10 hours to 20 hours. The excess borane is destroyed by quenching the mixture with water and 3a is recovered by concentrating the mixture by evaporation, diluting the concentrate with more water if necessary, and extracting 3a with a water immiscible solvent such as methylene chloride. The recovered 3a is of sufficient purity to use directly in the cyclization to 4a, however, it may be further purified prior to use by recrystallization.

The L-alcohol 3a is then cyclized to the (S)-4-aryloxazolidin-2-one (4a) in an inert solvent with n-butyllithium or an alkali metal alkoxide such as lithium or sodium ethoxide. n-Butyllithium is the preferred base and is generally used in less than the stoichiometric amount. The reaction is carried out for from 2 to 8 hours at a temperature between about 25° C. and about 65° C. and preferably at about 55° C. Suitable inert solvents are tetrahydrofuran, 1,2-dimethoxyethane and like ethers. After completion of the cyclization, the reaction mixture is treated with acetic acid in an amount corresponding to the amount of base used, and is concentrated. The oxazolidin-2-one(4a) is recovered from the concentrate by extraction with a suitable organic solvent such as methylene chloride, chloroform, or trichloroethane.

The (S)-4-aryloxazolidin-2-one (4a) is N-alkylated with a haloacetic acid ester, the ester deesterified, and the acid converted to the acyl halide 5a.

The alkylation of 4a with the haloacetic acid ester is carried out in dimethylformamide or tetrahydrofuran with sodium hydride to provide the (S)-4-aryloxazolidin-2-one-3-ylacetic acid ester. The haloacetic acid ester is represented by the formula X-CH$_2$COOalk in the foregoing reaction scheme, wherein X is chloro or bromo and alk is $C_1$-$C_4$ alkyl. Preferably, alk is t-butyl or ethyl. Examples of haloacetic acid esters are t-butyl bromoacetate, ethyl bromoacetate, methyl chloroacetate, t-butyl chloroacetate, methyl bromoacetate, isopropyl bromoacetate, and like esters. Preferred halo esters are t-butyl bromoacetate and ethyl bromoacetate.

The deesterification of the oxazolidinone acetic acid ester is achieved by standard deesterification procedures. For example, the t-butyl ester group is removed upon treatment of the ester with trifluoroacetic acid while other lower alkyl esters such as the ethyl ester can be saponified.

The oxazolidinone acetic acid is converted to the acid halide (5a, X'=halogen), preferably the acid chloride, the anhydride formed with trifluoroacetic acid (X'=O-COCF$_3$), or with a phosphoryl halide (X'=—O—P(-=O)X$_2$). The acid halide, preferably the chloride, is a preferred source of the ketene for use in the subsequent cycloaddition reaction. The acid chloride is obtained for example with oxalyl chloride in an inert solvent such as benzene, toluene, or xylene. Other conventional acid halide forming reagents may be used.

The (S)-4-aryloxazolidin-2-one-3-ylacetyl halide or anhydride is the functionalized form of the chiral auxiliary moiety used to form the β-lactam ring of the azetidinone intermediates represented by the formula 1.

The acetyl halide (5a) is allowed to react with the imine formed with a benzylamine and a 3-arylacrolein to form the 1-benzyl-3β-[(S)-4-aryloxazolidin-2-one-3-yl]-4β-(2-arylvinyl)azetidinone (formula 1, Y=—CH=CH). A minor amount of isomeric cycloaddition product is also formed. The cycloaddition reaction is illustrated in the following reaction scheme

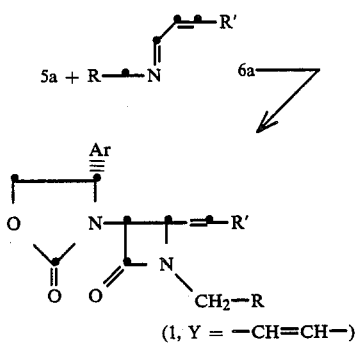

(1, Y = —CH=CH—)

wherein R, R' and Ar have the same meanings as defined for formula 1.

The reaction is carried out at a temperature between about −78° C. and about 25° C. in an inert organic solvent, such as methylene chloride, chloroform, toluene, or a di- or trichloroethane in the presence of a tri-($C_1$–$C_4$ alkyl)amine. A solution of the imine (6a) is added to a solution of 5a in an inert solvent containing the tri-($C_1$–$C_4$ alkyl)amine in an amount in excess of the stoichiometric amount. The tri-($C_1$–$C_4$ alkyl)amine is added to the solution of 5a prior to addition of the imine 6a. The acid derivative 5a and the amine are mixed at a temperature between about −80° C. and about −50° C. to form in situ the ketene. The imine 6a is then added to form the azetidinone 1. Conveniently, the solvent for the imine is the solvent in which it was prepared as described hereinbelow. Such solvents as benzene, toluene, and the xylenes are suitable. Following the addition of the imine, the reaction is warmed and maintained at about 0° C. for from 2 to 4 hours. The mixture of the major isomer (formula 1) and the minor isomer is recovered from the reaction mixture as follows. The reaction mixture is diluted with a water immiscible organic solvent such as methylene chloride or chloroform and is first washed with a weak acid such as tartaric acid or citric acid followed by a wash with saturated aqueous alkali metal bicarbonate. After drying, the washed mixture is evaporated to dryness. Most often the major isomer 1 can be crystallized from the residue from ethyl acetate-hexanes (ca 30% hexanes by volume). Alternatively, the major isomer can be separated from the minor isomer by chromatography over silica by using step-wise elution or gradient elution. Step-wise elution with ethyl acetate-methylene chloride with a percentage ethyl acetate by volume of from ca 20% will generally elute 1 while increased polarity (ca 40%–50% ethyl acetate by volume) will elute the minor component. After chromatography 1 can be recrystallized to enhance its purity.

The imine 6a employed in the cycloaddition is obtained by condensing a 3-arylacrolein with benzylamine or a substituted benzylamine in a suitable solvent. The water produced during the reaction is removed either by using a drying agent or by azeotropic distillation. A small excess over the stoichimetric amount of the acrolein is preferably used. Drying agents such as magnesium sulfate or molecular sieves are suitable. Organic solvents such as diethyl ether or an aromatic hydrocarbon such as benzene or toluene can be employed.

The condensation to form the imine proceeds rapidly at a temperature between about 25° C. and 65° C. in the presence of a drying agent or during azeotropic removal of water.

Examples of 3-arylacroleins which can be used are represented by the formula

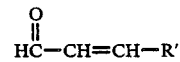

wherein R' is phenyl, $C_1$–$C_4$ alkylphenyl, $C_1$–$C_4$ alkoxyphenyl, halophenyl, furyl or naphthyl. Examples of such aldehydes are cinnamaldehyde, 4-methylcinnaldehyde, 3-ethylcinnamaldehyde, 4-ethoxycinnamaldehyde, 3-methoxycinnamaldehyde, 3-t-butyloxycinnamaldehyde, 3-ethoxycinnamaldehyde, 3-bromocinnamaldehyde, 2-(2-furyl)acrolein, 2-(2-naphthyl)acrolein, and like aldehydes.

Examples of benzylamines useful in the imine formation are benzylamine and the $C_1$–$C_4$ alkyl, $C_1$–$C_4$ alkoxy, and halo-substituted benzylamines such as 4-methylbenzylamine, 3-chlorobenzylamine, 3,4-dichlorobenzylamine, 4-methoxybenzylamine, 2-bromobenzylamine, 3-ethylbenzylamine, 3,4-dimethylbenzylamine, 2,4-dimethylbenzylamine, 4-chloro-3-methylbenzylamine, 4-isopropylbenzylamine, 4-t-butylbenzylamine, and the like.

The imine 6a can be employed in the cycloaddition reaction without prior isolation. For example, the reaction mixture in which the imine is prepared may be used directly in the cycloaddition to form 1.

The azetidinone represented by the formula 1, wherein Y is —CH=CH— and R' is a m-alkoxyphenyl group, is a valuable intermediate in a process provided by this invention for the asymmetric preparation of 1-carbacephalosporins. In particular the process comprises the preparation of 1-carba-3-hydroxy-3-cephem-4-carboxylic acid esters.

According to the process the (S)-4-aryloxazolidin-2-one-3-ylacetyl halide (5a) is reacted in the cycloaddition reaction described above with the imine (6a), formed with a benzylamine and a m-alkoxycinnamaldehyde, to provide the azetidinone represented by the formula 1 wherein Y is —CH=CH— and R' is a m-$C_1$–$C_4$ alkoxyphenyl group. The azetidinone 1 is hydrogenated to the corresponding 4β-[2-(m-alkoxyphenyl)ethyl]azetidinone, and the latter is reduced with lithium-ammonia in the presence of t-butyl alcohol to effect reduction of the phenyl ring, removal of the chiral auxiliary and the 1-benzyl group to provide a 3β-amino-4β-[2-(5-alkoxycyclohex-1,4-dienyl)ethyl]azetidinone. The 3-amino group of the azetidinone is protected with a conventional amino-protecting group and the 3β-protected-aminoazetidinone is subjected to ozonolysis to yield the β-keto ester $C_1$–$C_4$ alkyl 5-[3β-(protected amino)azetidin-2-one-4β-yl]-3-oxopentanoate.

The β-keto ester ozonolysis product is converted to the a-diazo derivative and the diazo derivative is cyclized with Rhodium II to provide the 3-hydroxy-1-carbacephalosporin ester.

The process is illustrated in the following reaction scheme

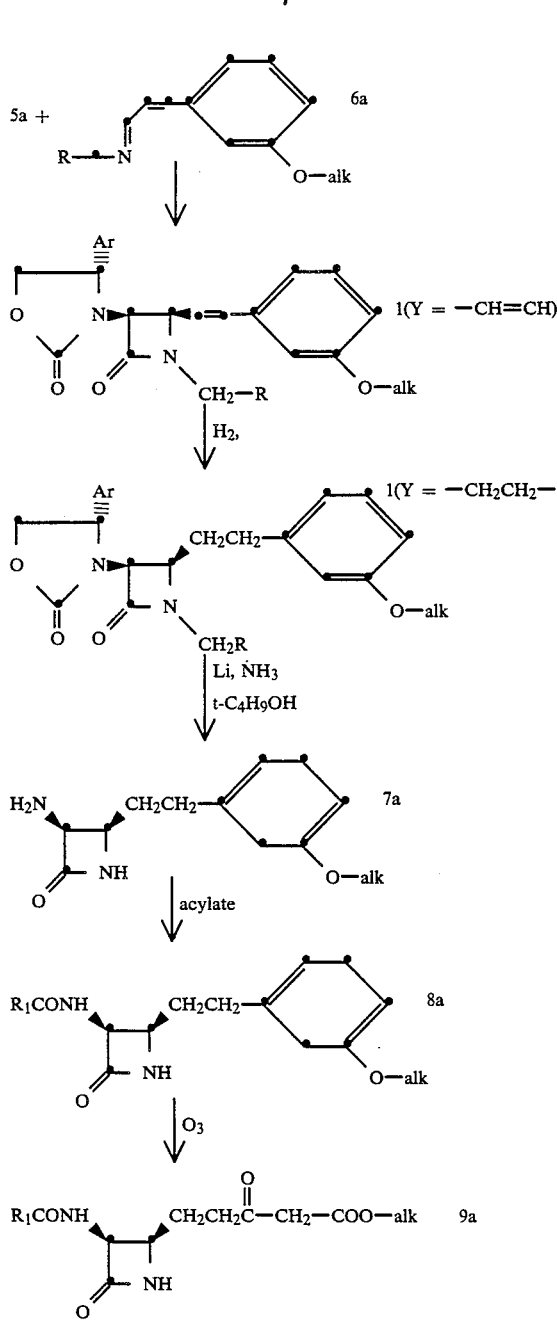

It will be appreciated with reference to the foregoing reaction scheme that the imine 6a is structurally selective in the process. The m-alkoxyphenyl group of the imine ultimately provides the alkyl β-ketoester 9a via ozonolysis of the 5-alkoxycyclohexa-1,4-diene 8a which in turn is provided by the lithium in ammonium reduction of 1 wherein Y=—CH₂—CH₂—.

According to this process the azetidinone 1 Y=—CH=CH—) is hydrogenated over a palladium catalyst such as a supported palladium catalyst eg. 5% or 10% palladium on carbon, barium carbonate, or other suitable support. The reduction can be carried out at atmospheric pressure, or at somewhat elevated pressures, in an inert solvent at room temperature. Inert solvents such as methylene chloride, di- or trichloroethane, tetrahydrofuran, methyl alcohol, ethyl alcohol, or ethyl acetate may be used.

The 4β-[2-(m-alkoxyphenyl)ethyl]azetidinone is reduced to the 3β-amino-4β-[2-(5-alkoxycyclohex-1,4-dienyl)ethyl]azetidin-2-one (7a) with lithium in liquid ammonia containing t-butyl alcohol. The reduction is carried out at a temperature between about −30° C. and about −90° C. and preferably at between about −70° C. and about −80° C. The reduction is carried out by dissolving lithium in liquid ammonia and cooling the solution to about −50° C. and about −90° C. An excess of t-butyl alcohol is added followed by the addition of a solution of the azetidinone in an inert solvent. The solution of the azetidinone may contain t-butyl alcohol as a cosolvent. Suitable solvents for the azetidinone include tetrahydrofuran, dimethoxyethane, or like solvent.

After the solution of the azetidinone is added, the reduction mixture is stirred for about 30 minutes to about 2 hours. On small laboratory size reactions, the reduction is allowed to stir in the cold for about 30 minutes while with large scale reductions in manufacture somewhat longer reduction time may be required for complete reduction to the diene 7a.

The reduction effects the removal of the chiral auxiliary moiety, incorporated via the cycloaddition with 6a, leaving the 3-amino group. The reduction also effects removal of the 1-benzyl or 1-substituted benzyl group.

The 3-aminoazetidinone 7a can be isolated from the reduction mixture and used in the next step after amino group protection as shown in the reaction scheme. Alternatively, and preferably in the process context, 7a is acylated in the same reaction vessel to provide the acylated aminoazetidinone 8a. Following the reduction the reaction mixture is treated with sufficient benzene to discharge the blue color of the mixture. Ammonium acetate is added to the mixture and the bulk of the ammonia is distilled off. The solvent and any remaining ammonia are evaporated. The residue 7a is treated with a water miscible organic solvent such as tetrahydrofuran and the mixture or solution is acidified to a pH between about 7 and about 9. The solution of 7a is then treated with an acylating agent to provide the 3β-acylamino-4β-[2-(5-alkoxycyclohex-1,4-dienyl)ethyl]azetidinone 8a. The 3β-amino group is acylated to protect its integrity during the subsequent ozonolysis step in the process.

The acylating agent may be formed with any carboxylic acid, the acyl residue of which is stable in the subsequent ozonolysis step of the process. The carboxylic acid can be for example an alkylcarboxylic acid such as acetic acid, propionic acid, butyric acid and the like; an arylcarboxylic acid such as benzoic acid, napthoic acid, which may be optionally substituted by lower alkyl, lower alkoxy, or halogen; or an arylacetic acid such as phenylacetic acid, phenoxyacetic acid, phenylthioacetic acid, and such acids optionally substituted. The desired carboxylic acid for use in the acylation is converted to an active derivative such as the acid chloride, acid anhydride or anhydride formed with a halo formate such as a C₁-C₄ alkyl chloroformate e.g. ethyl chloroformate and iso-butyl chloroformate. The acylating agent can be an aryloxycarbonyl halide such as benzyloxycarbonyl chloride or p-nitrobenzyloxycarbonyl chloride.

Preferred acylating agents are represented by the formula

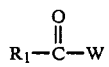

wherein $R_1$ is $C_1-C_6$ alkyl; a phenyl group

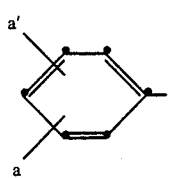

wherein a and a' independently are hydrogen, $C_1-C_4$ alkyl, $C_1-C_4$ alkoxy or halogen; a group represented by the formula

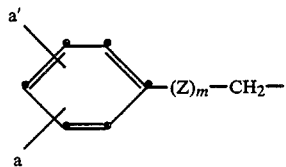

wherein Z is O or S, m is 0 or 1, and a and a' have the same meanings as defined above; or $R_1$ is $R°_1O$ wherein $R°_1$ represents $C_1-C_4$ alkyl, $C_5-C_7$ cycloalkyl, benzyl, nitrobenzyl, methoxybenzyl, or halobenzyl; and W is chloro, bromo, or an anhydride forming group represented by the formula

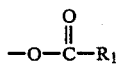

wherein $R_1$ has the same meanings as defined above.

Examples of acyl halides represented by the above formula are acetyl chloride, acetyl bromide, butyryl chloride, propionyl chloride, benzoyl chloride, 4-chlorobenzoyl chloride, 4-methylbenzoyl chloride, phenoxyacetyl chloride, 4-chlorophenoxyacetyl chloride, phenylacetyl chloride, 3-ethylphenylacetyl bromide, phenylmercaptoacetyl chloride, 4-chlorophenylmercaptoacetyl chloride, benzyloxycarbonyl chloride, cyclohexyoxycarbonyl chloride, cyclopentyloxycarbonyl chloride, ethoxycarbonyl chloride, and the like.

Examples of anhydrides represented by the above formula are benzoic acid anhydride, phenoxyacetic acid anhydride, phenylacetic acid anhydride, p-chlorophenoxyacetic acid anhydride, phenylmercaptoacetic acid anhydride, di-t-butyl dicarbonate, dibenzyl dicarbonate, di-(p-nitrobenzyl) dicarbonate, di-ethyl dicarbonate, di-cyclohexyl dicarbonate, and like anhydrides.

The N-acylated reduction product 8a is recovered from the mixture by extraction and is purified by chromatography over silica.

In an alternative to the above described preferred one-pot conversion of $1(Y=-CH_2CH_2-)$ to 8a, compound 1 is reduced with lithium in liquid ammonia without added t-butyl alcohol to provide the 3-aminoazetidinone represented by the formula

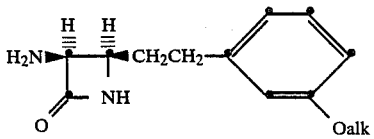

Acylation of the 3β-amino group with the desired carboxylic acid or amino-protecting group followed by reduction with lithium in liquid ammonia in the presence of excess t-butyl alcohol provides the 5-alkoxycyclohex-1,4-diene 8a.

Preferably the above-described alternative reduction with lithium in ammonia is carried out by using only about 3 equivalents of t-butyl alcohol rather than an excess. When the reduction is carried out with equivalents of t-butyl alcohol over a short reaction time the aromatic phenyl ring remains intact while the chiral auxiliary and N-benzyl group are removed. When the reduction is carried out as described above without added t-butyl alcohol incomplete removal of the 1-benzyl group and the chiral auxiliary can result.

The 3-acylaminoazetidinone 8a, obtained by either route, is then converted to the β-keto ester 9a by ozonolysis. The ozonolysis is preferably carried out in 50% methyl alcohol in dichloromethane or other suitable solvent mixture, at a temperature between about $-5°$ C. and about $-80°$ C. The ozone is passed into the solution of the diene 8a until the reaction is complete. The ozone is most conveniently obtained from a conventional ozone generator in a stream of air. The completion of the ozonolysis may be determined by the use of a diene indicator such as solvent red (Sudan III, Aldrich Chemical Company). Following completion any ozonide and excess ozone is destroyed in the cold with dimethyl sulfide or other suitable reducing agent such as a sulfite or phosphite and the product 9a is recovered from the mixture. For example, the reaction mixture is allowed to warm to room temperature, is poured into brine and the product is extracted with a water immiscible solvent such as methylene chloride. The β-keto ester 9a may be further purified by chromatography over silica.

The β-keto ester 9a is then converted to the 7-acylamino-1-carba(1-dethia)-3-hydroxy-3-cephem ester 11a via diazo compound 10a, and cyclization of the diazo ester to the 1-carbacephalosporin with rhodium II.

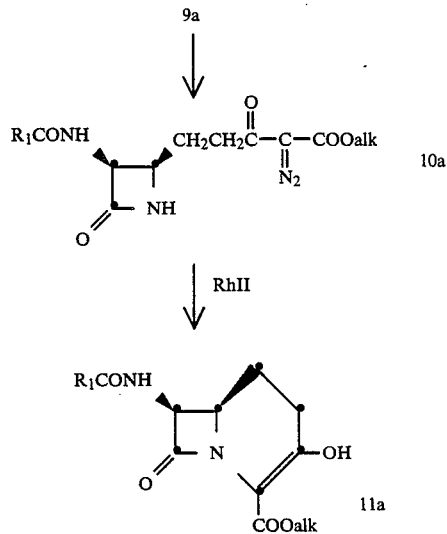

The β-keto ester 9a is best converted to the diazo ester 10a in an inert solvent such as acetonitrile, dichloromethane, trichloroethane, or the like, with p-toluenesulfonyl azide (tosyl azide) in the presence of a hindered tertiary amine, eg. diisopropylethylamine. The reaction is carried at conveniently at room temperature. Generally the tosyl azide is used in an excess of the stoichiometric amount while the amine is used in an amount of about one-fourth of the stoichiometric amount. The diazo ester is recovered from the reaction mixture by partitioning the mixture between a water immiscible solvent such as methylene chloride and brine containing some tartaric acid or citric acid. The diazo ester is obtained in purified form from the extract via chromatography over silica an recrystallization.

The ester moiety "alk" of 10a becomes the ester group of the 1-carbacephalosporin 11a upon cyclization as shown in the reaction scheme. Ester groups such as the lower n-alkyl groups e.g. methyl, and ethyl, are less readily removed form the carboxy function than other groups. From a synthetic point of view, it may be desirable to form a 1-carbacephalosporin 11a wherein the ester group is a conventional carboxy-protecting group more readily removed than methyl or ethyl. A further aspect of this invention provides a process for the transesterification of the ester group (alk) of 10a to diazo ester 10b as shown below.

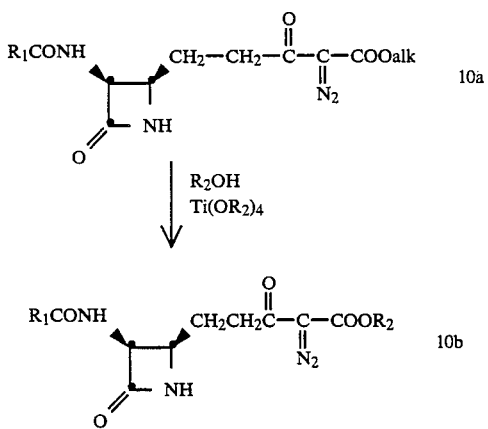

wherein $R_1$ and alk have the previously defined meanings and $R_2$ is allyl, 2,2,2-trichloroethyl, 2,2,2-tribromoethyl, $\beta$-tri($C_1$-$C_4$ alkyl)silylethyl, benzyl, $C_1$-$C_4$ alkylbenzyl, $C_1$-$C_4$ alkoxybenzyl, nitrobenzyl, or chlorobenzyl.

The process is carried out by mixing an excess of the alcohol, $R_2OH$, with titanium tetraisopropoxide and removing isopropyl alcohol by evaporation. The diazo ester, 10a, is added to the solution of the $Ti(OR_2)_4$ in excess alcohol, and an inert solvent if necessary, and the solution is maintained at a temperature between about 25° C. and about 45° C. until transesterification is complete.

Inert solvents which may be used are, for example, methylene chloride, di- or trichlorethane, chloroform, acetonitrile, tetrahydrofuran, or dioxane. When benzyl alcohol is used in the process to form the $R_2$ ester group it also may serve as a solvent for the process.

The diazo ester 10a or the diazo ester 10b obtained via the transesterification process is then cyclized to 1-carbacephalosporin 11a with rhodium II acetate in chloroform at the reflux temperature. The reaction is heated for about 15 minutes to about one hour and the 7-acylamino-3-hydroxy-1-carba(1-dethia)-3-cephemcarboxylic acid ester is recovered as such from the reaction mixture or is converted to a derivative which is then isolated.

The 3-hydroxy 1-carbacephalosporin ester may be recovered from the reaction mixture by first diluting the mixture with water or brine, acidifying the mixture, and then extracting the mixture with a solvent such as ethyl acetate or methylene chloride. The extract is washed, dried and evaporated to provide the product. The product may be further purified by chromatography and recrystallization.

In a preferred embodiment of the process L-phenylglycine (1a, Ar=phenyl) is converted to the ethylcarbamate with ethyl chloroformate, the carbamate acid is reduced with borane-dimethyl sulfide to L-1-ethoxycarbonylamino-1-phenylethanol (3a, alk=ethyl), and the phenylethanol is cyclized with n-butyllithium to (S)-4-phenyloxazolidin-2-one 4a. The latter is converted to 5a via alkylation with ethyl bromoacetate, saponification, and treatment of the acid with oxalyl chloride.

The (S)-4-phenyloxazolidin-2-one-3-ylacetyl chloride is condensed with the imine formed with benzylamine and m-methoxycinnamaldehyde (form 6a, alk=methyl, R=phenyl) to form the azetidinone 1, Ar=phenyl, alk=methyl). Catalytic reduction of 1 over 5% Pd-C provides 1, ($Y=CH_2-CH_2-$) which on reduction in lithium in liquid ammonia and t-butyl alcohol yields the 3-aminoazetidinone (7a, alk=methyl). Without isolation, the 3-aminoazetidinone is acylated with di-(t-butyl) dicarbonate to form the 3-t-butyloxycarbonylaminoazetidinone (8a, $R_1$=t-butyloxy, alk=methyl). Ozonolysis of the 3-t-BOC amino protected diene product in 50% methyl alcohol in dichloromethane provides the $\beta$-keto methyl ester 9a. The $\beta$-keto methyl ester is reacted in acetonitrile with tosyl azide in the presence of diisopropylethylamine to provide the diazo methyl ester (10a, $R_1$=t-butyloxy, alk=methyl). The transesterification of the diazo methyl ester to the corresponding benzyl ester is carried out in excess benzyl alcohol with titanium tetra-isopropoxide with heating at about 36° C. for 42 hours. The diazo benzyl ester is treated in refluxing chloroform with rhodium (II) acetate to provide benzyl 7$\beta$-(t-butyloxycarbonylamino)-3-hydroxy-1-carba(1-dethia)-3-cephem-4-carboxylate.

In another embodiment of the process L-phenylglycine is converted to 3$\beta$-(4(S)-phenyloxazolidin-2-one-3-yl)-4$\beta$-[2-(m-methoxyphenyl)ethyl]-1-benzylazetidin-2-one, the latter reduced with lithium in liquid ammonia and t-butyl alcohol and the reduction product, 3$\beta$-amino-4$\beta$-[2-(5-methoxycyclohex-1,4-diene)ethyl]azetidin-2-one (7a, alk=methyl) without isolation is acylated with phenoxyacetic acid anhydride. The 3$\beta$-phenoxyacetylaminoazetidinone is then converted, as described above for the t-BOC amino-protected azetidinone, to benzyl 7$\beta$-phenoxyacetylamino-3-hydroxy-1-carba(1-dethia)-3-cephem-4-carboxylate.

The azetidinone represented by the formula 1, wherein Y is $-CH=CH-$ and R' is furyl, also is useful as an intermediate in the preparation of 1-carbacephalosporins. Accordingly, this intermediate is hydrogenated in a suitable solvent to the corresponding 3$\beta$-(2-furylethyl)azetidinone (formula 1, $Y=-CH_2-CH_2-$, R'=furyl) over 5% palladium on carbon. The hydrogenation product is converted to the 1-carbacephalosporin as shown in the following scheme

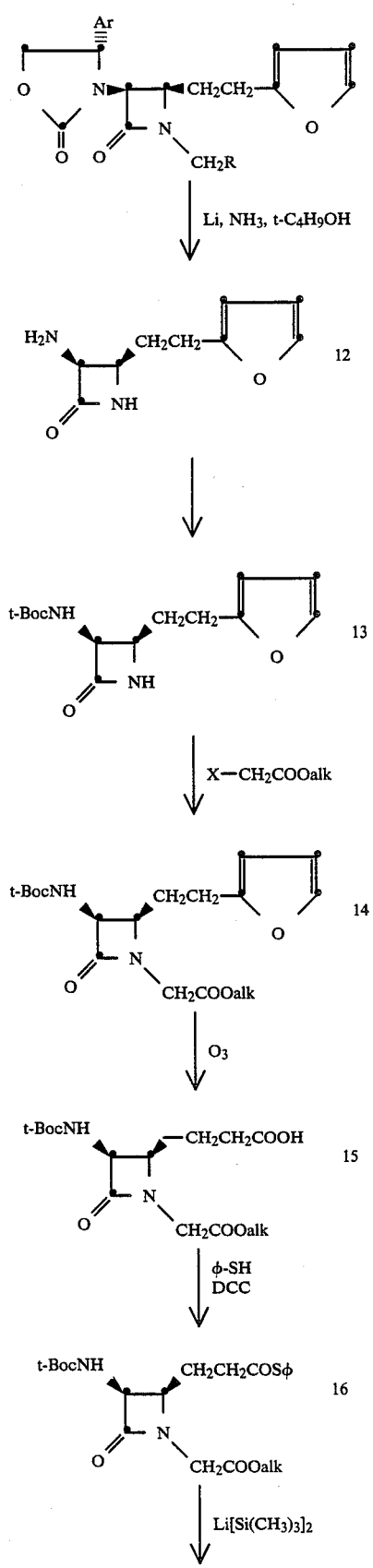

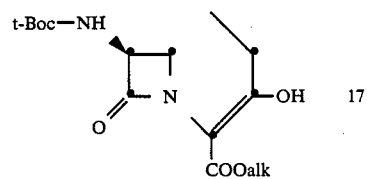

The hydrogenation product is first reduced molar equivalents of t-butyl alcohol to provide the 3β-aminoazetidinone 12, and the amino group is protected with a conventional protecting group such as the t-butoxycarbonyl group to yield 13. N-Alkylation of 13 with an alkyl haloacetate, eg t-butyl bromoacetate, affords 14. Ozonolysis of 14 provides the 2-carboxyethyl N-alkylated protected aminoazetidinone 15. Formation of the phenylthio ester of 15 with thiophenol and dicyclohexylcarbodiimide is followed by cyclization to the 3-hydroxy-1-carbacephalosporin ester 17 with lithium hexamethyldisilazane.

The 3-hydroxy-1-carbacephalosporin ester 17 can be treated to remove the amino-protecting group to provide the nucleus ester 7β-amino-3-hydroxy-1-carba(1-dethia)-3-cephem-4-carboxylic acid ester. The latter can be acylated with the desired carboxylic acid derivative, eg. phenylacetyl chloride or phenoxyacetyl chloride, and then treated with diazomethane to form the 7β-acylamino-3-methoxy-1-carba(1-dethia)-3-cephem-4-carboxylic acid ester. The ester is deesterified to yield the free acid antibiotic compound.

The azetidinones represented by the formula 1, wherein Y is —CH=CH—, also are useful intermediates in the preparation of the monocyclic β-lactam antibiotic, 3β-[2-(2-aminothiazol-4-yl)-2-(carboxymethoxyimino)acetamido]-3β-carbamoyloxymethylazetidin-2-one-1-sulfate, described by U.S. Pat. No. 4,502,994. The azetidinone is subjected to ozonolysis to form the 4β-formylazetidinone as shown below

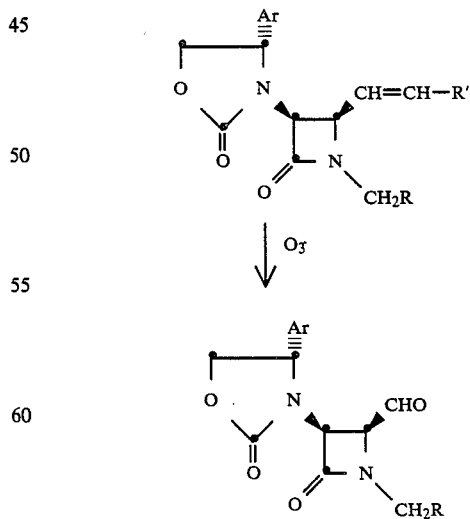

The 3β-formyl azetidinone is reduced with sodium borohydride to the corresponding 3β-hydroxymethyl substituted azetidinone represented by the formula

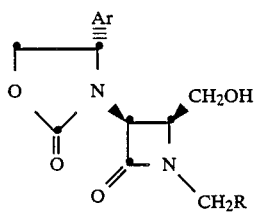

In the above formulae Ar, R' and R have the same meanings as defined for formula 1.

The 3β-hydroxymethyl compound is reduced with lithium in liquid ammonia containing about 3 equivalents of t-butyl alcohol to yield the 3β-amino-4β-hydroxymethylazetidin-2-one represented by the formula

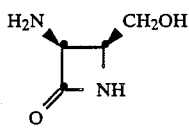

The amino group is protected with a conventional aminoprotecting group such as the benzyloxycarbonyl group or the t-butyloxycarbonyl group and the hydroxy group of the 4β-hydroxymethyl substituent is protected for example by esterification with a lower alkanoic acid chloride such as acetyl chloride, chloroacetyl chloride, or trichloroacetyl chloride. The di-protected compound then is reacted with $SO_3$ in pyridine to form the azetidinone represented by the formula

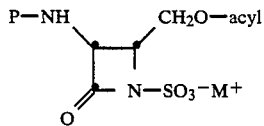

wherein P is a conventional amino-protecting group, acyl is the acyl moiety of a lower alkanoic acid and $M^+$ is an alkali metal cation or a tetraalkylammonium ion such as tetrabutylammonium ion.

The hydroxy-protecting acyl group is removed by basic hydrolysis and the product reacted with an isocyanate to provide the compound represented by the formula

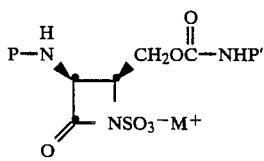

wherein P' is for example an acyl group such as trichloroacetyl or trifluoroacetyl. Removal of the amino protecting group P, the carbamoyl N-protecting group P', and reacylation of the 3β-amino group with an active carboxy derivative of a 2-(2-protected-aminothiazol-4-yl)-2-(protected-carboxymethoxyimino)acetic acid provides the di-protected antibiotic. Removal of the protecting groups affords the sulfazecin related antibiotic represented by the formula.

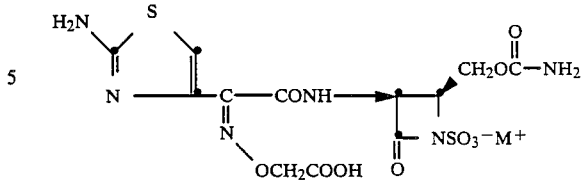

The 4β-formylazetidinone of the above formula also may be converted to the corresponding 4β-carboxyazetidinone by oxidation e.g. with chromium trioxide-$H_2SO_4$ in acetone or with acidic permanganate or other suitable reagent. The carboxy group may be esterified to a $C_2$–$C_4$ alkyl ester and the latter reduced with sodium borohydride or lithium aluminum hydride to the 4β-hydroxymethylazetidinone. The 4β-carboxyazetidinone in the form of a lower alkxl ester may be epimerized with a t-alkylamine to the 4α-carboxyazetidinone ester and the latter reduced to the 4α-hydroxymethyl azetidinone.

The epimeric 4-hydroxymethylazetidinones may be converted individually to the 4-halomethyl azetidinone, eg. the bromomethyl or iodomethyl derivative and the latter reduced with lithium aluminum hydride to the corresponding epimeric 4-methylazetidinone.

The 4-methylazetidinones thus obtained can be subjected to lithium in ammonia reduction with t-butyl alcohol to remove the chiral auxillary and the 1-benzyl group to provide the 3β-amino-4-methylazetidinone. The latter is converted by known methods to the monocyclic antibiotic, monobactam, represented by the formula

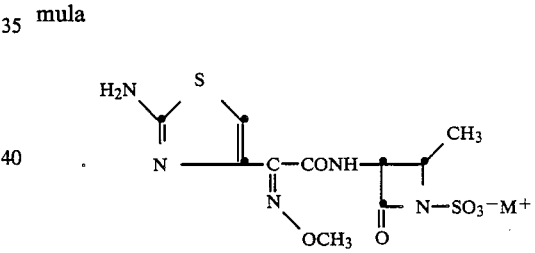

In a further aspect of this invention there is provided substituted azetidinones represented by the formula

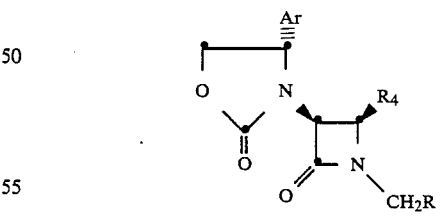

wherein R4 is formyl, carboxy, $C_1$–$C_4$ alkoxycarbonyl, methyl, halomethyl, or hydroxymethyl and Ar and R have the same meanings as defined for formula 1 above and when R4 is other than formyl, the 4-position epimers thereof.

A preferred group of substituted azetidinones are represented when Ar is phenyl or substituted phenyl, R is phenyl, and R4 is formyl or hydroxymethyl. A preferred compound is 1-benzyl-3β-[(S)-4-phenyloxazolidin-2-one-3-yl]-4β-hydroxymethylazetidin-2-one. Another preferred compound is 1-benzyl-3β-[(S)-4-phenyloxazolidin-2-one-3-yl]-4β-formylazetidin-2-one.

The intermediates useful in the asymmetric synthesis of the azetidinones of formula 1 described above are also part of the invention. The 4(S)-aryloxazolidin-2-one-3-ylacetic acids, esters, and halides represented by the formula 5a are useful in the process as chiral auxiliary forming moieties upon cyclization with the imine 6a to form the azetidinone 1. The chiral auxiliary functions in the process to direct the synthesis of 1 to the desired stereo configuration. These acyl halides, anhydrides, and the ester and acid precursors thereof are represented by the formula

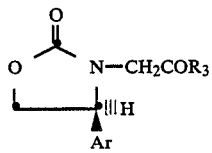

wherein Ar has the same meanings as defined for formula 1, and $R_3$ is hydroxy, $C_1$-$C_4$ alkoxy, chloro, bromo, trifluoroacetoxy, or —O—P(=O)$X_2$.

Examples of the above intermediates are 4(S)-phenyloxazolidin-2-one-3-ylacetic acid, 4(S)-(4-chlorophenyl)oxazolidin-2-one-3-ylacetic acid, 4(S)-(4-methylphenyl)oxazolidin-2-one-3yl-acetic acid, 4(S)-(3-methoxyphenyl)oxazolidin-2-one-3yl-acetic acid, 4(S)-(2-naphthyl)oxazolidin-2-one-3yl-acetic acid, 4(S)-(2-thienyl) oxazolidin-2-one-3yl-acetic acid, 4(S)-(benzothien-2-yl)oxazolidin-2-one-3yl-acetic acid, and the $C_1$-$C_4$ alkyl esters, the acyl chloride and bromide, and the trifluoroacetic acid and phosphoryl halide derivatives thereof. Preferred compounds are represented when Ar is phenyl or substituted phenyl, and $R_3$ is t-butyl or chloro. Especially preferred compounds are 4(S)-phenyloxazolidin-2-one-3-ylacetic acid, the ethyl and t-butyl esters and the acid chloride thereof.

The 5-alkoxycyclohex-1,4-dienyl substituted azetidinones (formulae 7a and 8a) are also novel intermediates and are represented by the following formula

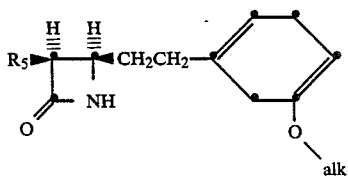

wherein $R_5$ is amino or an acylamino group $R_1$—CO— wherein $R_1$ has the same meanings as defined hereinabove with reference to formula 8a, and alk is $C_1$-$C_4$ alkyl. In the above formula alk is preferably methyl.

Examples of $R_1$CO acyl groups when $R_1$ is an alkoxy, cycloalkoxy or benzyloxy group are ethoxycarbonyl, t-butyloxycarbonyl, cyclopentyloxycarbonyl, cyclohexyoxycarbonyl, benzyloxycarbonyl, and p-nitrobenzyloxycarbonyl, and the like.

Examples of $R_1$CO acyl groups when $R_1$ (formula 8a) is other than $R_1°$ are phenylacetyl, phenoxyacetyl, phenylmercaptoacetyl, benzoyl, p-chlorobenzoyl, 2,6-dimethoxybenzoyl, 4-chlorophenylmercaptoacetyl, 3,4-dimethylphenylacetyl, 4-methoxyphenylacetyl, and 3-chlorophenoxyacetyl.

The 3β-aminoazetidinones of the above formula wherein $R_5$ is amino can form salts with suitable inorganic and organic acids. Examples of such acids are hydrochloric acid, hydrobromic, sulfuric acid and phosphoric acid, and the alkyl and aryl sulfonic acids such as a $C_1$-$C_4$ alkylsulfonic acid, eg. methanesulfonic acid and n-butylsulfonic acid; arylsulfonic acids, eg. benzenesulfonic acid, p-toluenesulfonic acid, p-chlorophenylsulfonic acid, p-bromobenzenesulfonic acid, and naphthalenesulfonic acid.

The following Examples are provided to further illustrate the invention. In the Examples compound numbers refer to the numbered compounds in the reaction schemes.

PREPARATION 1

(S)-4-Phenyloxazolidin-2-one

To a stirred, 0° C. solution of L-phenylglycine (25.3 g, 167.4 mmol) in 60 mL of 3N aqueous NaOH was added ethyl chloroformate (8 mL) in several portions. Additional 3N aqueous NaOH (35 mL) was added to redissolve the precipitated phenylglycine, followed by ethyl chloroformate (4 mL). This process was continued with 3N aqueous NaOH (65 mL) and ethyl chloroformate (8 mL, total of 20 mL, 209 mmol) over a period of ca. 10 minutes. After stirring for 1 hour at 0° C. the solution was acidified with 6M $H_2SO_4$, and the precipitated carbamate was extracted into 8% isopropanol in dichloromethane (2×300 mL). The combined organic layers were dried ($Na_2SO_4$) and concentrated to afford 37.3 g of N-ethoxycarbonyl L-phenylglycine as a white solid. The carbamate was dissolved in 170 mL of THF, cooled to 0° C., treated with borane-dimethylsulfide (33.5 mL of a 10M solution), and stirred at room temperature for 17 hours. Excess borane was cautiously quenched with water (100 mL), and the bulk of the THF removed under reduced pressure. The white slurry was diluted with additional water (350 mL) and then extracted with dichloromethane (2×500 mL). The combined organic layers were washed with 100 mL of saturated aqueous $NaHCO_3$, dried ($Na_2SO_4$), and concentrated to give 27.4 g of (S)-2-ethoxycarbonylamino-2-phenylethanol as a white solid. The crude alcohol was dissolved in 200 mL of THF, cooled to 0° C., and treated with n-butyllithium in hexane (6 mL of a 2M solution). After heating at 55° C. for 6 hours, the solution was treated with acetic acid (1 ml) and concentrated. The residue was dissolved in dichloromethane (300 mL), washed with 100 mL of brine, dried ($Na_2SO_4$), and concentrated to a white solid. Recrystallization from toluene gave 17.14 g (63%) of (S)-4-phenyloxazolidin-2-one; mp 132°-133° C.; $[\alpha]_D^{20}$ +49.5° (c=2.1, $CHCl_3$); IR ($CHCl_3$) 3460, 3020, 1760, 1500, 1480, 1460, 1400, 1230 cm$^{-1}$; $^1$HNMR δ 7.45-7.30 (m, 5, ArH), 6.42 (br s, 1, NH), 4.96 (br t, 1, J=7.8 Hz, OCH$_2$CH), 4.72 (t, 1, J=8.6 Hz, one of OCH$_2$CH), 4.17 (dd, 1, J=6.7, 8.7 Hz; one of OCH$_2$CH).

Anal. Calcd for $C_9H_9NO_2$: C, 66.24; H, 5.56. Found: C, 66.16; H, 5.62.

PREPARATION 2

(S)-4-Phenyloxazolidin-2-one-3-ylacetic acid

To a stirred, 0° C. solution of (S)-4-phenyloxazoldin-2-one (1.07 g, 6.54 mmol) in 15 mL of THF was added sodium hydride (0.32 g of a 60% oil dispersion, 8.0 mmol). When gas evolution had ceased (ca. 10 minutes), ethyl bromoacetate (0.87 mL, 7.8 mmol) was added. After 2 hours at 0° C., the mixture was treated with 50 mL of 2N aqueous NaOH, stirred rapidly for 1 hour at room temperature, and then partitioned between hexane (50 mL) and water (50 mL). The aqueous layer was separated, acidified with 6M aqueous H₂SO₄, and extracted with dichloromethane (2×200 mL). The combined organic phases were dried (Na₂SO₄) and concentrated to a thick oil, which was dissolved in 4 mL of warm toluene, seeded, and allowed to crystallize overnight; filtration gave 1.33 g (92%) of (S)-4-phenyloxazolidin-2-one-3-ylacetic acid: mp 106°–108° C.; $[\alpha]_D^{22}$+173° (c=2.0, CHCl₃); IR (CHCl₃) 3500–2500 (v. br), 1760 (br), 1480, 1460, 1430, 1230 cm⁻¹; ²H NMR δ11.2 (br s, 1, COOH), 7.47–7.25 (m, 5, ArH), 5.05 (t, 1, J=8.4 Hz, OCH₂CH), 4.72 (t, 1, J=8.8 Hz, one of OCH₂CH), 4.32 (d, 1, J=18.4 Hz, one of NCH₂), 4.17 (t, 1, J=8.4 Hz, one of OCH₂CH), 3.41 (d, 1, J=18.4 Hz, one of NCH₂).

Anal. Calcd for C₁₁H₁₁NO₄: C, 59.72; H, 5.01. Found: C, 59.83; H, 5.00.

PREPARATION 3

(S)-4-phenyloxazolidin-2-one-3-ylacetyl chloride:

A 250 mL round bottom flask fitted with a reflux condenser and a CaSO₄ drying tube was charged with (S)-4-phenyloxazolidin-2-one-3-ylacetic acid (5.3 g, 23.96 mmol) and 60 mL of toluene. The suspension was treated with oxalyl chloride (3.2 mL, 36.7 mmol) and stirred at 60° C. for 3 hours. At this point gas evolution had ceased and the reaction was homogeneous. Removal of solvent under reduced pressure afforded the title acid chloride as a thick oil.

PREPARATION 4

Preparation of imine formed from benzylamine and 3-methoxycinnamaldehyde:

To a solution of 3-methoxycinnamaldehyde (4.27 g, 26.33 mmol) in 40 mL of toluene was added benzylamine (2.73 mL, 25.01 mmol). The solution was warmed briefly to ca. 40° C., and upon cooling became cloudy from released water. Argon flushed 4A molecular sieves (18 g, freshly activated) were added and the mixture was allowed to stand at room temperature for 16 hours. This solution of imine was used directly in the subsequent cyclization.

EXAMPLE 1

Formation of 1-benzyl-3β-[(S)-4-phenyloxazolidin-2-one-3-yl]-4β-(3-methoxystyryl) azetidin-2-one:

The oxazolidinone acid chloride was dissolved in dichloromethane (70 mL), cooled to −78° C., and treated with triethylamine (5.0 mL, 35.9 mmol). A fine, heavy precipitate formed over 15 minutes. To this mixture was added, via cannula, the toluene solution of the imine prepared as described above. The sieves from the imine solution were washed with dichloromethane (2×10 mL), and each wash added to the reaction. The cold bath was removed, the reaction warmed and maintained at 0° C. for 2 hours. The mixture was poured into 200 mL of dichloromethane, washed with 0.5M tartaric acid and saturated aqueous NaHCO₃ (50 mL each), dried (Na₂SO₄), and concentrated to a reddish oil. Crystallization from ca. 150 mL of 30% hexanes in ethyl acetate gave 6.87 g of the title compound as white needles. Chromatography of the mother liquor on 170 g of slica with 20% ethyl acetate in dichloromethane gave an additional 1.9 g of the azetidinone (total 8.77 g, 80%). The minor isomer was obtained by further elution with 40% ethyl acetate in dichloromethane and was then purified by chromatography on silica with 30% hexanes in ethyl acetate.

Major isomer, the title compound: mp 142°–143° C.; $[\alpha]_D^{22}$+46.4° (c=1.0, CHCl₃); IR (CHCl₃) 3020, 1760, 1600, 1410 cm⁻¹; ¹H NMR (CDCl₃) δ7.45–6.75 (m, 14, ArH), 6.45 (d, 1, J=16 Hz, ArCH=CH), 5.81 (dd, 1, J=16, 8.9 Hz, ArCH=CH), 4.88 (dd, 1, J=8.9, 7.4 Hz, OCH₂CH), 4.61 (t, 1, J=8.9 Hz, one of OCH₂CH), 4.55 (d, 1, J=5 Hz, C₃H), 4.53 (d, 1, J=14.7 Hz, one of ArCH), 4.23–4.12 (m, 3, one of ArCH₂, one of OCH₂CH, C₄H), 3.82 (s, 3, OCH₃).

Anal. Calcd for C₂₈H₂₆N₂O₄: C, 73.99; H, 5.77. Found: C, 74.06; H, 5.74.

EXAMPLE 2

By using the method described in Example 1, the imine prepared from benzylamine and cinnamaldehyde, and 4(S)-phenyloxazolidin-2-one-3-ylacetyl chloride there was prepared 1-benzyl-3β-[4(S)-phenyloxazolidine-2-one-3-yl]-4β-styrylazetidine-2-one: mp 186.5°–187.5° C.; $[\alpha]_D^{22}$=+56.9° (c=1.7, CHCl₃); IR (CHCl₃) 3010, 1760, 1500, 1460, 1410 cm⁻¹; ¹H NMR (CDCl₃) δ7.45–7.10 (m, 15, ArH), 6.48 (d, 1, J=16 Hz, CH=CH—Ar), 5.87 (dd, 1, J=9, 16 Hz, CH=CH—Ar), 4.88 (dd, 1, J=7.4, 8.9 Hz, OCH₂CH), 4.61 (t, 1, J=8.9, one of OCH₂CH), 4.55 (d, 1, J=16 Hz, one of ArCH₂), 4.54 (d, 1, J=4.7 Hz, C-3 H, overlaps with doublet at 4.55), 4.21 (dd, 1, J=4.7, 9.0 Hz, C-4 RH), 4.17 (dd, J=7.4, 8.9 Hz, one of OCH₂CH), 4.14 (d, 1, J=16 Hz, one of ArCH₂).

Anal. Calcd. for C₂₇H₂₄N₂O₃: C, 76.39; H, 5.70. Found: C, 76.53; H, 5.69.

EXAMPLE 3

By using the method described in Example 1, the imine prepared from benzylamine and 3-(2-furyl)acrolein was condensed with 4(S)-phenyloxazolidin-2-one-3-ylacetyl chloride to provide 1-benzyl-3β-[4(S)-phenyloxazolidine-2-one-3-yl]-4β-[2-(2-furyl)ethenyl]-azetidine-2-one: mp 181°–182° C.; $[\alpha]_D^{20}$=+13.6° (c=1.6, CHCl₃), IR (CHCl₃) 3020, 1760, 1660, 1500, 1460, 1410 cm⁻¹; ¹H NMR (CDCl₃) δ7.45–7.07 (m, 11, ArH), 6.39 (dd, 1, J=1.8, 3.3 Hz, OCH=CH), 6.27 (d, 1, J=16 Hz, N—CH—CH=CH), 6.25 (d, 1, J=3.3 Hz, O—C=CH), 5.75 (dd, 1, J=16, 8.9 Hz, N—CH—CH=CH), 4.91 (dd, 1, J=8.8, 7.4 Hz, OCH₂CH), 4.65 (t, 1, J=8.9 Hz, one of OCH₂CH), 4.61 (d, 1, J=15 Hz, one of ArCH₂), 4.55 (d, 1, J=4.8 Hz, C-3 H), 4.20 (dd, 1, J=7.4, 8.8 Hz, one of OCH₂CH), 4.11 (dd, 1, J=4.8, 8.9 Hz, C-4 H), 4.02 (d, 1, J=15 Hz, one of ArCH₂).

Anal. Calcd. for C₂₅H₂₂N₂O₄: C, 72.44; H, 5.35. Found: C, 72.44; H, 5.41.

EXAMPLE 4

1-Benzyl-3β-[(S)-4-phenyloxazolidin-2-one-3-yl]-4β-[2-(3-methoxyphenyl)ethyl]azetidin-2-one The 3-methoxystyryl substituted azetidinone prepared as described in Example 1 (0.552 g, 1.22 mmol) was hydrogenated (balloon pressure) in dichloromethane (20 mL) over 0.052 g of 5% Pd on carbon for 3 hours at room temperature. Filtration through celite and removal of solvent under reduced pressure afforded 0.555 g (100%) of the corresponding 4β-[2-(3-methoxyphenyl)ethyl]azetidinone (compound 8) as a white solid. Recrystallization from hexanes-ethyl acetate gave long needles: mp 134°–135° C.; $[\alpha]_D^{23}$+38.6° (c=2.2, CHCl$_3$); IR (CHCl$_3$) 3010, 1755, 1605, 1590, 1410 cm$^{-1}$; $^1$H NMR δ7.44–6.42 (m, 14, ArH), 4.97–4.84 (br t, 1, OCH$_2$CH), 4.68 (t, 1, J=9 Hz, one of OCH$_2$), 4.64–4.59 (br d, 1, C$_3$H), 4.32 (s, 2, ArCH$_2$), 4.27 (dd, 1, J=6.4, 9.0 Hz, one of OCH$_2$), 3.77 (s, 3, OCH$_3$), 3.57 (dt, 1, J=6.6, 4.9 Hz, C$_4$H), 2.36 (br t, 1, J=8 Hz, ArCH$_2$CH$_2$), 1.56–1.44 (br q, 1, ArCH$_2$CH$_2$).

Anal. Calcd for C$_{20}$H$_{24}$N$_4$O$_6$: C, 73.66; H, 6.18. Found: C, 73.48; H, 6.11.

EXAMPLE 5

Methyl 5-[3β-(t-butyloxycarbonylamino)azetidin-2-one-4β-yl]-3-oxopentanoate

Lithium wire (0.548 g, 79 mmol) was added to 55 ml of ammonia at −78° C. and the mixture was warmed briefly to affect solution of the metal and then recooled to −78° C. under positive argon pressure. The dark blue solution was first treated with tert-butanol (12 mL). A solution of the 1-benzyl-3β-(4-phenyloxazolidin-2-one-3-yl)-4β-[2-(3-methoxyphenyl)ethyl] azetidin-2-one (2.36 g, 5.17 mmol) in THF:tert-butanol (24 mL of a 3:1 mixture) was then added via cannula over a period of 5 minutes. After stirring for exactly 30 additional minutes, dry benzene (2 mL) was added. The blue color discharged after ca. 1 minute. Ammonium acetate (6.08 g, 79 mmol) was added, the cold bath removed, and the bulk of the ammonia was distilled off through a mercury bubbler. Solvent and any residual ammonia were removed under reduced pressure at 40° C. The remaining white solid was suspended in 50 mL of THF:H$_2$O (1:1), acidified to pH 8 with 3N HCl, and treated with di-tert-butyl dicarbonate (1.8 mL, 7.8 mmol). The two phase mixture was stirred rapidly for 12 hours and then partitioned between dichloromethane (200 mL) and H$_2$O (50 mL). The aqueous phase was reextracted with dichloromethane (50 mL) and the combined organic phases were washed with 50 mL of saturated aqueous NaHCO$_3$, dried (Na$_2$SO$_4$), and concentrated. Chromatography of the residue on 110 g of silica with 40% hexanes in ethyl acetate afforded 1.23 g of the partially purified dihydroaromatic 3β-t-butyloxycarbonylamino-4β-[2-(5-methoxycyclohex-1,4-diene)ethyl]azetidine-2-one as a waxy solid.

The diene product was dissolved in 25 mL of 50% methanol in dichloromethane, treated with one drop of pyridine and ca. 1 mg of Sudan III dye (Aldrich Chemical Co.), and ozonolyzed at −78° C. until the red color discharged. Dimethyl sulfide (3 mL) was added, the cold bath removed, and the reaction mixture stirred at room temperature for 5 hr. The light orange solution was poured into 100 Lm of brine and extracted with dichloromethane (1×200 mL, 1×50 mL). The combined organic layers were dried (Na$_2$SO$_4$) and concentrated. Chromatography of the residue on 65 g of silica with 7% isopropanol in dichloromethane afforded methyl 5-[3β-(t-butyloxycarbonylamino)azetidin-2-one-4β-yl]-3-oxopentanoate (0.97 g, 60% from 8) as an off white solid. Recrystallization from toluene gave colorless needles: mp 122°–123° C.; [α$_D^{20}$ +48.6° (c=1.4, CHCl$_3$); IR (CHCl$_3$) 3430, 3420, 3340 (br), 3020, 2990, 1770, 1720, 1510, 1370, 1250, 1160 cm$^{-1}$; $^1$H NMR (CDCl$_3$) δ6.51 (br s, 1, NH of β-lactam), 5.50 (br d, 1, BocNH), 5.05–4.98 (m, 1, C-3H), 3.83–3.71 (m, 1, C-4H), 3.75 (s, 3, OCH$_3$), 3.48 (s, 2, COCH$_2$CO), 2.74–2.56 (m, 2, CH$_2$CH$_2$CO), 1.93–1.74 (m, 2, CH$_2$CH$_2$CO), 1.45 (s, 9, tert-butyl).

Anal. Calcd. for C$_{14}$H$_{22}$N$_2$O$_6$: C, 53.49; H, 7.06. Found: C, 53.56; H, 7.11.

The 3-t-BOC-aminoazetidinyl β-keto ester prepared as described above was then converted to the 3-hydroxy-1-carba(1-dethia)-3-cephem ester by the procedures of the following Example 6.

EXAMPLE 6

Benzyl 7β-(t-butyloxycarbonylamino)-3-trifluoromethylsulfonyloxy-1-carba(1-dethia)-3-cephem-4-carboxylate A. Diazo Transfer To a 0° C. solution of the β-keto ester (1.13 g, 3.6 mmol) in 10 mL of acetonitrile was added p-toluenesulfonyl azide (3.6 mL of a 1.5M solution in dichloromethane) and diisopropylethylamine (0.13 mL, 0.75 mmol). The reaction was covered with foil, stirred at room temperature for 2 hours, and then partitioned between dichloromethane (100 mL) and brine (50 mL) containing 10 mL of 0.5 M tartaric acid. The aqueous layer was reextracted with dichloromethane (50 mL) and the combined organic layers dried (Na$_2$SO$_4$) and concentrated. Chromatography of the residue on 100 g of silica with 5% isopropanol in dichloromethane afforded 1.15 g (94%) of the diazo keto ester as a white solid. Recrystallization from ethyl acetate-hexanes gave small needles: mp 136°–137° C. (dec); [α]$_D^{20}$ +65.8° (c=0.6, CHCl$_3$); IR (CHCl$_3$) 3440, 3420, 3360 (br), 3020, 2990, 2150, 1770, 1720, 1650, 1510, 1440, 1370, 1320, 1160 cm$^{-1}$; $^1$H NMR δ6.49 (br s, 1, NH of β-lactam); 5.46 (d, 1, J=8.6, BocNH); 5.06 (dd, 1, J=4.8 Hz, 8.1 Hz; C$_3$H); 3.85 (s, 3, OCH$_3$); 3.85–3.78 (m, 1, C$_4$H); 3.06–2.82 (m, 2, CH$_2$CH$_2$CO); 2.0–1.75 (m, 2, CH$_2$CH$_2$CO); 1.45 (s, 9, tert-butyl).

Anal. Calcd. for C$_{14}$H$_{20}$N$_4$O$_6$: C, 49.40; H, 5.92. Found: C, 49.47; H, 5.93.

B. Transesterification

A solution of benzyl alcohol (20 mL, 193 mmol) and titanium isopropoxide (0.78 mL, 2.62 mmol) was stirred under vacuum (1 mm Hg) for 45 minutes to remove isopropanol. The flask was covered with foil, vented to argon, and the diazo β-keto methyl ester (0.953 g, 2.80 mmol) was added. the solution was heated at 36° C. for 42 hours, diluted with 60 mL of diethyl ether, and treated with saturated aqueous Na$_2$SO$_4$ (3 mL). The mixture was stirred rapidly overnight, and then filtered through a pad of celite. After removal of ether on a rotary evaporator, the benzyl alcohol was distilled off using a kugelrohr oven (15 millitorr, 50° C.). Chromatography of the residue on 100 g of silica afforded the corresponding diazo β-keto benzyl ester (0.837 g, 72%) as a white solid: mp 152–153 (dec); [α]$_D^{20}$ +55.6° (c=0.7, CHCl$_3$); IR (CHCl$_3$) 3450, 3420, 3350 (br), 3020, 2990, 2150, 1770, 1715, 1655, 1510, 1370, 1305, 1165 cm$^{-1}$; $^1$H NMR δ7.45–7.3 (m, 5, ArH), 6.4 (br s, 1, NH of β-lactam), 5.40 (d, 1, J=8.6, BocNH), 5.26 (s, 2, ArCH$_2$), 5.06 (br dd, 1, J=4.5 Hz, 8.5 Hz; C$_3$H); 3.79 (dt, J=4.5, 8.5 Hz, C$_4$H), 3.05–2.82 (m, 2, CH$_2$CH$_2$CO); 2.0–1.73 (m, 2, CH$_2$CH$_2$CO); 1.45 (s, 9, tert-butyl).

Anal. Calcd. for C$_{20}$H$_{24}$N$_4$O$_6$: C, 57.68; H, 5.81. Found: C, 57.57; H, 5.74.

C. Cyclization Rhodium (II)

A solution of the diazo β-keto benzyl ester (0.12 g, 0.29 mmol) in 6 mL of alumina filtered chloroform was heated to reflux and treated with rhodium (II) acetate dimer (1.5 mg, 0.0034 mmol). After heating for 20 minutes, the mixture was placed in an ice bath, and treated sequentially with diisopropylethyl amine (0.10 mL, 0.6 mmol) and trifluoromethanesulfonic anhydride (0.049 mL, 0.29 mmol). The reaction was maintained at 0° C. for 15 minutes and then partitioned between dichloromethane (75 mL) and 0.5 M aqueous tartaric acid (25 mL). The organic layer was dried ($Na_2SO_4$) and concentrated to a light red oil, which was chromatographed on 20 g of silica with 6% ethyl acetate in dichloromethane to afford benzyl 7β-(t-butyloxycarbonylamino)-3-trifluoromethylsulfonyloxy-1-carba(1-dethia)-3-cephem-4-carboxylate (0.118 g, 78%) as a hard, colorless foam: $[\alpha]_D^{20}$ +31.5° (c=0.5, $CHCl_3$); IR ($CHCl_3$) 3420, 3010 2990, 1790, 1725, 1505, 1435, 1250, 1160, 1140 $cm^{-1}$; $^1H$ NMR ($CDCl_3$) δ7.46–7.3 (m, 5, ArH), 5.39 and 5.25 (two d (AB), 2, J=12.1 Hz, $ArCH_2$), 5.22–5.10 (m, 2, BocNH and C7H), 3.86 (dt, 1, J ca. 4.2, 11.9 Hz, $C_6H$), 2.63 (dd, 2, J=4.0, 8.8 Hz, C=$CCH_2$), 2.20–2.08 and 1.78–1.60 (m, 2, $CH-CH_2$), 1.44 (s, 9, tert-butyl).

Anal. Calcd. for $C_{21}H_{23}N_2F_3O_8S$: C, 48.46; H, 4.45. Found: C, 48.61; H, 4.49.

EXAMPLE 7

Benzyl 7β-phenoxyacetylamino-3-trifluoromethylsulfonyloxy-1-carba(1-dethia)-3-cephem-4-carboxylate To a solution of the 7β-t-butyloxyaminocarbacephalosporin (0.12 g, 0.23 mmol) prepared as described in Example 6, in 1 mL of anisole was added 2 mL of trifluoroacetic acid. After 30 minutes the solution was concentrated under reduced pressure (1 mm Hg) to an off-white solid. Phenoxyacetic anhydride (0.094 g, 0.33 mmol) and dichloromethane (2.5 mL) were added to the solid, the mixture cooled to 0° C. and treated with diisopropylethyl amine (0.13 mL, 0.75 mmol). The solution was stirred for 30 minutes and then partitioned between 0.5N aqueous tartaric acid (50 mL) and dichloromethane (75 mL). The organic phase was washed with saturated aqueous $NaHCO_3$, dried ($Na_2SO_4$), and concentrated to an oil. Chromatography on 20 g of silica gel with 6% ethyl acetate in dichloromethane afforded 0.115 g (90%) of benzyl 7β-phenoxyacetylamino-3-trifluoromethanesulfonyloxy-1-carba(1-dethia)-3-cephem-4-carboxylate as a hard foam: $[\alpha]_D^{23}$+35 8° (c=0.6, $CHCl_3$); IR 3420, 3040, 1790, 1740, 1695, 1605, 1525, 1500, 1435, 1250 $cm^{-1}$; $^2H$ NMR ($CDCl_3$) 6 7.45–6.88 (m, 11, ArH and NH), 5.45–5.23 (m, 3, AB of $ArCH_2$ and C-7 H), 4.54 (s, 2, $ArOCH_2$), 3.94 (ddd, J=3.5, 5.1, 11.7 Hz, C-6 H), 2.65–2.57 (m, 2, $CHCH_2CH_2$), 2.10–1.98 and 1.70–1.54 (m, 2, $CHCH_2CH_2$).

EXAMPLE 8

1-Benzyl-3β-[4(S)-phenyloxazolidin-2-one-3yl]-4β-hydroxymethylazetidin-2-one

A solution of 1-benzyl-3β-[4(S)-phenyloxazolidin-2-one-3-yl)-4β-styryl-azetidin-2-one (3.0 g, 7.06 mmol) in 80 mL of 50% methanol in dichloromethane containing two drops of pyridine and a few milligrams of Sudan III dye (Aldrich Chemical Co.) was treated with a dilute mixture of ozone in oxygen at −78° C. When the red color of the dye was consumed, the ozone inlet was removed and 8 mL of dimethyl sulfide added. The solution was stirred for 3 hours at room temperature and then concentrated under reduced pressure. The oil was redissolved in 35 mL of ethanol, cooled to 0° C., and treated with sodium borohydride (0.40 g, 10.6 mmol). After ca. 15 minutes a heavy precipitate formed. Water 35 mL) was added and stirring continued at room temperature for another 30 minutes. Most of the ethanol was removed under reduced pressure and the remaining slurry partitioned between dichloromethane and water (200 mL each). The organic layer was dried ($Na_2SO_4$) and concentrated to a white solid. Recrystallization from ethyl acetate - dichloromethane (first crop, 1.887 g) and ethyl acetate - hexanes (second crop, 0.501 g) gave 2.388 g (96%) of 1-benzyl-3β-[4(S)-phenyloxazolidin-2-one-3-yl]-4β-hydroxymethyl-azetidine-2-one as white needles: mp 159.5°–160.0° C.; $[\alpha]_D^{23}$ +109.1° (c=2.2, $CHCl_3$); IR 3450 (br), 3010, 1760, 1500, 1480, 1460, 1410 $cm^{-1}$; H NMR ($CDCl_3$) δ7.50–7.00 (m, 10, ArH), 5.09 (dd, 1, J=6.5, 9.1 Hz, $ArCHCH_2$), 4.74 (t, 1, J=9.0 Hz, one of $ArCHCH_2$), 4.49, (d, 1, J=4.7 Hz, C-3 H), 4.32–4.26 (m, 3, AB pattern of $ArCH_2N$ and one of $ArCHCH_2$), 3.71 (dt, 1, J=5.0, 7.2 Hz, C-4 H); 3.56–3.34 (m, 2, $CH_2OH$), 2.32 (dd, 1, J=5.1, 6.5 Hz, OH).

EXAMPLE 9

3β-Benzyloxycarbonylamino-4β-hydroxymethylazetidin-2-one

The 4β-hydroxymethylazetidinone (0.497 g, 1.41 mmol) was dissolved with warming in 8 ml of 7:1 THF:tert-butanol and added to a −78° C. solution of lithium (0.087 g, 12.6 mmol) in 23 mL of anhydrous ammonia over 2 mintues. After stirring for an additional 2 minutes the excess lithium was quenched with 2 mL of 50% tert-butanol in benzene. Powdered ammonium chloride (0.68 g, 12.7 mmol) was added and the ammonia was allowed to distill off. Solvent, and any remaining ammonia, were then removed under reduced pressure. The residue was dissolved in water (15 mL), acidified briefly to pH 3 with 1N aqueous $NaHSO_4$, and then basified to pH 8 with 3N aqueous NaOH. Benzyl chloroformate (0.42 ml, 3.0 mmol) was added, and the reaction stirred at room temperature, using aqueous sodium hydroxide to maintain the pH at ca 8. After 3 hours excess benzyl chloroformate was destroyed with aqueous ammonia and the mixture extracted with dichloromethane (1×150 mL, 1× 50 mL). The organic layers were dried ($Na_2SO_4$) and concentrated. Chromatography on 35 g of silica with 12% isopropanol in dichloromethane afforded 0.219 g (62%) of 3β-benzyloxycarbonylamino-4β-hydroxymethyl-azetidine-2-one as a white solid. Recrystallization from hexanes - ethyl acetate gave an analytical sample: mp 128.5°–129.5° C.; $[\alpha]_D^{23}$=+7.1° (c=1.0, $CHCl_3$); IR ($CHCl_3$) 3400 (v br), 3010, 2950, 1765, 1720, 1520, 1320, 1230. 1050 $cm^{-1}$; $^1H$ NMR ($CDCl_3$) δ7.33 (s, 5, ArH), 6.94 (s, 1, NH of β-lactam), 6.32 (d, 1, J=10Hz, NH at C-3), 5.14 (dd, 1, J=4.9, 10.0 Hz, C-3 H), 5.07 (s; 2, $ArCH_2$), 3.85–3.55 (m, 4, C-4 H, $CH_2OH$).

EXAMPLE 10

1-Benzyl-3β-(4(S)-phenyloxazolidin-2-one-3-yl)-4β-[2-(2-furyl)ethyl]azetidin-2-one The product obtained as described by Example 3, (0.5 g) was dissolved in 10 ml of methylene chloride and was hydrogenated at room temperature for one hour under 50 psi hydrogen pressure in the presence of 0.05 g of 5% palladium on carbon. The reduction mixture was filtered and the clear filtrate was evaporated to provide the title compound as a white solid.

EXAMPLE 11

3β-t-Butyloxycarbonylamino-4β-[2-(2-furyl)ethyl]azetidin-2-one

A 500 ml 5-necked flask equipped with a nitrogen inlet, ammonia inlet, stirrer, thermometer, and drying tube was cooled under nitrogen to a temperature of about −70° C. in an acetone-dry ice bath. The ammonia was turned on, the nitrogen flow discontinued, and about 200 ml of ammonia were collected in the flask. Lithium (1.66 g, 240 mmole) cut in small pieces from lithium wire and washed under argon with benzene and diethyl ether was added to the ammonia.

To the blue lithium-ammonia solution was added dropwise over 4.5 minutes a solution of 10 g (24 mmole) of 1-benzyl-3β-[4(S)-phenyloxazolidin-2-one-3-yl]-4β[2-(2-furyl)ethyl]-azetidin-2-one in 80 ml of tetrahydrofuran containing 3.85 ml (72 mmole) of t-butyl alcohol. The temperature of the reaction mixture rose to −46° C. and the mixture was stirred for about 3 minutes. The reaction was quenched with 18.9 ml of 1,2-dichloroethane and 3.14 ml of acetic acid. The ammonia was evaporated by warming the mixture to room temperature and the THF was distilled off. THF was again added and distilled off to remove all ammonia. Aqueous THF was added to the residue of the product followed by 11.58 ml (48 mmole) of di-t-butyl dicarbonate and the mixture was stirred overnight at room temperature.

The two-phase reaction mixture was extracted with methylene chloride and the extract dried and evaporated to dryness. The residue was stirred with diethyl ether and the white solid filtered to yield 1.7 g of the product, 3β-t-butyloxycarbonylamino-4β-[2-(2-furyl)ethyl]azetidin-2-one as a white solid. An additional 900 mg of the product was obtained from the mother liquor by trituration with ether.

EXAMPLE 12

1-t-Butyloxycarbonylmethyl-3β-t-butyloxycarbonylamino-4β-[2-(2-furyl)ethyl]azetidin-2-one To a cold (−30° C.) solution of 1.2 g (4.3 mmole) of 3β-t-butyloxycarbonylamino-4β-[2-(2-furyl)ethyl]azetidin-2-one in 15 ml of DMF were added dropwise with stirring 1.94 ml of "Triton B". The mixture was stirred for 15 minutes at −30° C., warmed to 0° C. for 15 minutes, and recooled to −30° C. A solution of t-butyl bromoacetate in 3 ml of DMF was added dropwise and the mixture stirred at −30° C. for 15 minutes, 1 hour at 0° C. and at room temperature for 2 hours. Cold water was added to the mixture and the precipitate was filtered. The precipitate was washed with water to remove DMF and dried under vacuum to yield 1.2 g (71% yield) of the title compound as a white solid.

EXAMPLE 13

1-t-Butyloxycarbonylmethyl-3β-t-butyloxycarbonylamino-4β-(2-carboxyethyl)azetidin-2-one A 100 ml round bottom flask equipped with a magnetic stirrer, nitrogen inlet, ozone inlet, a sodium bisulfite scrubber, and a thermometer, was charged with a solution of 1.0 g of 1-t-butyloxycarbonylmethyl-3β-t-butyloxycarbonyl-amino-4β-[2-(2-furyl)ethyl]azetidin-2-one in 30 ml of methylene chloride:methyl alcohol 1:1, v:v, and cooled to −78° C. A few crystals of Sudan III red dye were added and a stream of ozone in air was bubbled through the solution until the red color was discharged (ca. 40 minutes). The cooling bath was removed and 1.56 ml of dimethylsulfide were added. The reaction mixture was warmed to room temperature and stirred for about 5 hours. The mixture was poured into aqueous sodium bicarbonate and the mixture washed with methylene chloride. The aqueous layer was acidified with hydrochloric acid and extracted with methylene chloride. The extract was washed with brine, dried over sodium sulfate and evaporated to yield 400 mg of the title compound as a foam.

EXAMPLE 14

1-t-Butyloxycarbonylmethyl-3β-t-butyloxycarbonylamino-4β-(2-phenylthiocarbonylethyl)azetidin-2-one To a cold (0° C.) solution of 350 mg of 1-t-butyloxycarbonylmethyl-3β-t-butyloxycarbonylamino-4β-(2-carboxyethyl)azetidin-2-one in 6 ml of methylene chloride containing 1 ml of DMF maintained under nitrogen were added 26 mg of dimethylaminopyridine, 0.308 ml of thiophenol, and 212 mg of dicyclohexylcarbodiimide (DCC). The mixture was stirred in the cold for 10 minutes and at room temperature for 1 hour. An additional 45 mg of DCC were added and stirring was continued for 2 hours. After standing overnight, the mixture was poured into 40 ml of methylene chloride and the mixture washed with an aqueous sodium bicarbonate solution (50% of saturated), with 0.1N hydrochloric acid, and with a saturated sodium bicarbonate solution. The solution was dried over sodium sulfate and evaporated to dryness to yield the title compound as a partly crystalline oil.

EXAMPLE 15 t-Butyl 7β-t-butyloxycarbonylamino-3-hydroxy-1-carba(1-dethia)-3-cephem-4-carboxylate To a solution of 4.4 g (9.47 mmole) of the azetidinone phenylthio ester, prepared according to the method described in Example 14 in 100 ml of dry THF and maintained under argon at −78° C. is added 29.5 ml (3.12 mmol) of lithium hexamethyldisilazane. After about 15 minutes the mixture is poured into 750 ml of aqueous ammonium chloride (50% of saturation) and the pH is adjusted to 3 with 1N hydrochloric acid. The acidified mixture is extracted three times with 50 ml portions of methylene chloride, the extracts combined, washed with brine, dried over sodium sulfate and concentrated by evaporation. The concentrate is initially chromatographed over silica using hexane-ethyl acetate, ca 3:1, v:v followed by a 1:1, v:v. mixture of the same solvents for elution of the product. The eluate is evaporated to dryness to provide the title compound.

We claim:

1. A compound of the formula

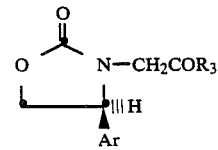

wherein Ar is phenyl, $C_1$–$C_4$ alkylphenyl, halophenyl, $C_1$–$C_4$ alkoxyphenyl, naphthyl, thienyl, furyl, benzothienyl, or benzofuryl; and $R_3$ is hydroxy, $C_1$–$C_4$ alkoxy, chloro, bromo, trifluoroacetoxy, or —O—P(=O)$X_2$ wherein X is chloro or bromo.

2. The compound of claim 1 wherein Ar is phenyl.

3. The compound of claim 2 wherein $R_3$ is $C_1$–$C_4$ alkoxy, chloro, or hydroxy.

4. The compound of claim 2 wherein $R_3$ is ethoxy or t-butyloxy.

* * * * *